United States Patent [19]

Chang

[11] Patent Number: 5,250,662
[45] Date of Patent: Oct. 5, 1993

[54] ALBUMIN PURIFICATION
[75] Inventor: Chong E. Chang, La Canada, Calif.
[73] Assignee: Alpha Therapeutic Corporation, Los Angeles, Calif.
[21] Appl. No.: 842,749
[22] Filed: Feb. 27, 1992

Related U.S. Application Data

[63] Continuation of Ser. No. 417,287, Oct. 5, 1989, abandoned.

[51] Int. Cl.$^5$ .................. C07K 3/22; C07K 15/06
[52] U.S. Cl. ........................... 530/364; 530/416
[58] Field of Search ............... 530/362, 363, 364, 416

[56] References Cited

U.S. PATENT DOCUMENTS

| | | | |
|---|---|---|---|
| 2,390,074 | 12/1945 | Cohn | 530/364 |
| 3,234,199 | 2/1966 | Reid | 530/380 |
| 4,075,197 | 2/1978 | Schuck et al. | 530/364 |
| 4,086,222 | 4/1978 | Lindquist et al. | 530/364 |
| 4,093,612 | 6/1978 | Travis et al. | 530/364 |
| 4,097,473 | 6/1978 | Lewis, Jr. et al. | 530/364 |
| 4,136,094 | 1/1979 | Condie | 530/364 |
| 4,228,154 | 10/1980 | Fisher et al. | 530/364 |
| 4,305,870 | 12/1982 | Liu et al. | 530/389.5 |
| 4,486,341 | 12/1984 | Chang | 530/380 |
| 4,675,384 | 6/1987 | Dromard et al. | 530/364 |
| 4,754,019 | 6/1988 | Gion et al. | 530/364 |
| 4,764,279 | 8/1988 | Tagot et al. | 210/656 |

FOREIGN PATENT DOCUMENTS

| | | |
|---|---|---|
| 1234047 | 3/1988 | Canada . |
| 0367220 | 5/1990 | European Pat. Off. . |
| 1471006 | 4/1977 | United Kingdom . |

OTHER PUBLICATIONS

Berglöf et al, J. Appl. Biochem., vol. 5 (4–5), pp. 282–292 (1983).
Cohn et al, "Separation into Fractions of Protein and Lipoprotein Components," *J. Am. Chem. Soc.*, 68, 459–475 (1946).
Roelands et al, "Effects of Repeated Heating on Human Albumin," *Vox Sang.*, 26, 415–424 (1974).
Solli et al, "Polymer Distribution in Human Serum Albumin Prepared by Lyophilization or Acetone Drying," *Vox Sang.*, 32, 239–241 (1977).
Ruckenstein et al, "Biotechnology Report: Protein Separation by Potential Barrier Chromatography," *Biotech. and Bioeng.*, 28, 432–451 (1986).
Nakamura et al, "Dynamic Analysis of Irreversible Adsorption of Protein on Porous Polymer Resins as Studied by Pulse Injection Method," *Biotech. and Bioeng.*, 30, 216–224 (1987).
Graham et al, "A Comparative Study of Models to Predict Protein Adsorption," *Biotech. Prog.*, 3, 141–145 (1987).
Schneider et al, "An Alternative Method of Large Scale Plasma Fractionation for the Isolation of Serum Albumin," *Blut*, Band 30, 121–134 (1975).
de Villiers et al, "Ethanol and Heath-Treated [sic] Plasma Fractionation Methods in South Africa," *Vox Sang.*, 35, 405–411 (1978).

(List continued on next page.)

*Primary Examiner*—Jeffrey E. Russel
*Attorney, Agent, or Firm*—Christie, Parker & Hale

[57] ABSTRACT

There is provided in accordance with the practice of this invention a process for separating albumin from an impure protein fraction containing albumin. Contaminants, in an aqueous solution of the impure protein fraction containing albumin, are precipitated from the solution at a pH of from about 4.5 to about 4.7. Additional contaminants that remain soluble are bound to an anion-exchange resin. After the precipitated and anion-exchange-bound contaminants are removed from the albumin-containing solution, the pH of the solution is adjusted to from about 4.7 to about 6.1, and additional contaminants are precipitated. Further contaminants are then bound to an anion-exchange resin, and these precipitated and anion-exchange-bound contaminants are removed from the albumin-containing solution.

16 Claims, No Drawings

OTHER PUBLICATIONS

Lima et al, "Contamination of Albumin by Alpha 1-Acid Glycoprotein," *Biochem. Pharmacol.*, 30, 2633–2636 (1981).

Eriksson et al, "Recovery of human albumin from Cohn fraction IV paste," presented at Joint Mtg. of 19th Congress of Int'l. Society of Haematology and the 17th Congress of Int'l. Society of Blood Transfusion, Budapest, Aug. 1–7, 1982.

Edsall, "Stabilization of Serum Albumin to Heat, and Inactivation of the Hepatitis Virus," *Vox Sang.*, 46, 338–340 (1984).

Tsou et al, "Prediction of Adsorption and Desorption of Protein on Dextran Based Ion-Exchange Resin," *AIChE Journal*, 31, 1959–1966 (1985).

Pinto et al, "Application of the Shrinking-Core Model for Predicting Protein Adsorption," *Reactive Polymers*, 5, 49–53 (1987).

Brochure published by Laboratory Separation Div., Pharmacia, Uppsala, Sweden, "Ion Exchange Chromatography: Principles and Methods," 10–17 (1986).

ALBUMIN PURIFICATION

CROSS REFERENCE TO RELATED APPLICATIONS

This is a continuation of application Ser. No. 07/417,287, filed Oct. 5, 1989, now abandoned.

FIELD OF THE INVENTION

This invention relates to a method useful for the separation of albumin from other proteins found in plasma.

BACKGROUND OF THE INVENTION

Albumin is the most abundant protein in blood plasma and is found at a concentration of approximately 35 to 55 grams per liter of plasma. Albumin normally is a monomer with a molecular weight of 66,000 to 69,000; however, it may also form polymers, with proportionally higher molecular weights. The most common method for purification of albumin from plasma is by the Cohn, cold ethanol precipitation, method (Cohn et al., *J. Amer. Chem. Soc.*, 68, 459-475 (1946); also U.S. Pat. No. 2,710,294). The Cohn method separates plasma proteins by sequential precipitations using increasing concentrations of cold ethanol and decreasing pH values. The fractions separated by this method are: Fraction I, Fraction II+III, Fraction IV$_1$, Fraction IV$_4$, and Fraction V. Most of the albumin present in plasma is in the Fraction V precipitate or paste.

The Fraction V albumin extracted from plasma by the Cohn method is estimated to be 95% pure (i.e., 95% by weight of the protein present in Fraction V is albumin). However, further purification of albumin is desirable, since pasteurization of the albumin solutions results in precipitation of a portion of the contaminating proteins, which adversely affects the clarity of the final albumin solutions.

Albumin's main uses are as a plasma extender and for correction of hypoproteinemia. In addition, albumin is frequently used: (1) as a stabilizing agent for other proteins contained in preparations administered for various medical treatments, such as Factor VIII; (2) to maintain the colloid osmotic pressure; and (3) for in vivo transport functions, for example, of fatty acids and drugs.

Methods that have been used to further purify albumin from Fraction V include: additional ethanol precipitations or acetone precipitations with heating. The yield of albumin from the additional ethanol precipitation method is relatively low, however, due to denaturation and loss of albumin during the precipitation procedure.

The acetone precipitation with heating method of purifying albumin uses two steps. The first step is to resuspend the albumin precipitate in acetone, where acetone-soluble contaminants remain in solution. The albumin precipitate is separated from the acetone-soluble contaminants by filtration, and the recovered albumin precipitate is redissolved in water. The second step is the heating step, during which additional impurities are removed. During the heating step, a portion of the remaining impurities precipitate, due to heat denaturation, while albumin, which is relatively stable to heat denaturation, remains in solution. This purification method also results in a low yield of albumin, mainly due to denaturation of a portion of the albumin. In addition, the heating step reduces the albumin monomer content and increases the albumin polymer content. High monomer contents are desired in the final albumin product, since it has been suggested that albumin polymers are cleared more rapidly from circulation than are albumin monomers, effectively resulting in a reduction in the concentration of infused albumin. It has also been suggested that the polymer form of albumin may produce an undesirable immunological response.

Other methods that have been used for the separation of albumin from the impurities in Fraction V have generally been by chromatography, and most commonly, by ion-exchange chromatography. Two general forms of ion-exchange chromatography are used. The first is by the use of cation-exchange resins, which contain a negatively-charged ligand attached to a support matrix, and the other is by use of anion-exchange resins, which contain a positively-charged ligand attached to a support matrix.

To determine if a protein will bind to an ion-exchange resin (either an anion- or a cation-exchange resin), the isoelectric point (pI) of the desired protein, the pH of the solution, and the salt concentration of the solution must be considered.

The pI of a protein is the pH at which there is a net zero charge on the protein. The pI values of proteins, which are specific for a particular protein, vary over the whole spectrum of the pH range. By varying the pH of a solution, the charge on a particular protein can be manipulated and utilized for the purification of a desired protein from contaminating proteins. When the pH of the solution containing the selected protein equals its pI, the net charge on the protein is zero, and the protein will not bind to either an anion- or a cation-exchange column. When the pH of the protein solution is decreased to below the pI of the selected protein, there will be a net positive charge on the protein which increases as the pH decreases. Under these conditions, proteins with a net positive charge will bind to a cation-exchange resin. The strength of binding to the resin is dependent on the total charge on the protein, i.e., if the PH is just below the pI of the protein, there will only be a small positive charge on the protein, and the binding to a cation-exchange resin will be very weak. If the pH of the solution is far below the pI of the protein, there will be a large positive charge on the protein, and the binding, to a cation-exchange resin, will be strong. When there is a net positive charge on the protein, the protein will have no affinity for an anion-exchange resin. Conversely, as the pH of the protein solution is increased above the pI of the protein, by the addition of alkali, there will be a negative charge on the protein which increases as the pH increases. As a result of this negative charge, the protein will be able to bind to an anion-exchange resin. The strength of the binding is dependent on the strength of the charge on the protein. A negatively-charged protein will have no affinity for a cation-exchange resin.

An additional effect of manipulating the pH of the solutions is that some proteins can be induced to precipitate. Many proteins are insoluble at pH values that approach their pI value. Many proteins will, therefore, precipitate from solution when the pH of the solution is adjusted to a value equal to their pI. Albumin remains soluble when pH values approach its pI.

Proteins, even when charged, can be prevented from binding to an ion-exchange resin by the presence of salt in the solution. In ion-exchange chromatography, salt competes with the charged protein for binding to the charged groups of the chromatography resin. When a protein has a small charge, the binding to the ion-exchange resin will be weak, and only low salt concentrations will be required to compete with the protein to prevent binding to the ion-exchange resin. Conversely, when a protein has a larger charge, the binding to the ion-exchange resin will be strong, and high salt concentrations will be required to compete with the protein to prevent binding to the ion-exchange resin.

In view of the foregoing, it can be seen that pH values can be chosen that will result in a protein having either a negative, positive, or zero charge, or that will make the protein insoluble, and salt concentrations can be chosen that will permit binding of a charged protein to an ion-exchange resin.

Although ion-exchange chromatography has previously been used to purify albumin, the known methods are undesirably expensive and inefficient. For example, in one method, the albumin (instead of contaminating proteins) is bound to the ion-exchange resin. This method requires the use of large amounts of resin to bind the large amounts of albumin present in the impure albumin solution. This results in undesirably-high resin costs and long reaction times.

A more efficient and economical method of purifying albumin by ion-exchange chromatography, is to bind the contaminants, which are present in the impure albumin solutions in much smaller amounts than albumin, to the resin. In prior-art processes in which contaminants are bound, both anion- and cation-exchange resins are used in combination. When these prior-art anion/cation procedures were used, salt, at concentrations up to 70 mm, was added to the albumin solutions. This method also results in an undesirably-high cost, since the added salt (1) must be removed prior to medical use of the albumin; and (2) prevents binding of some contaminants to the resin, resulting in undesirably-low purities of the final albumin solution.

None of the prior-art methods described above result in albumin solutions where greater than 99% of the protein present is albumin or where the albumin monomer content is desirably high. In addition, some contaminants, such as alpha-1-acid glycoprotein, have not been successfully removed from prior-art albumin concentrates. The presence of alpha-1-acid glycoprotein in the final albumin product is undesirable, since it has a high affinity for many basic drugs and, when infused with albumin, results in unpredictable circulating concentrations of such drugs.

Currently, the methods used to purify albumin result in final products having either undesirably-high proportions of albumin polymers, and/or undesirably-high levels of particulate matter, and/or an undesirably-low albumin purity. It is therefore desirable that there be provided a process for the separation of albumin monomer from other contaminating proteins found in impure albumin fractions, such as the Fraction V paste produced by the Cohn method.

SUMMARY OF THE INVENTION

The present invention is directed to a process for separating albumin from an impure protein fraction containing albumin and unwanted protein contaminants, for example, from Fraction V paste from the Cohn method, from other blood-plasma-derived fractions, or from recombinant-DNA-derived materials containing albumin. Albumin is separated by providing a first aqueous solution containing the impure protein fraction. The pH of the first aqueous solution is adjusted to a value of from about 4.5 to about 4.7, to precipitate protein contaminants. Soluble protein contaminants in the first aqueous solution are bound to an anion-exchange resin, and the precipitated and anion-exchange resin-bound contaminants are separated from the solution to thereby provide a second aqueous solution containing albumin. The pH of the second aqueous solution is adjusted to a value of from about 4.7 to about 6.1, to precipitate protein contaminants. Protein contaminants that are soluble in the second aqueous solution, are bound to an anion-exchange resin, and thereafter, the precipitated and anion-exchange resin-bound contaminants are separated from the solution to provide a third aqueous solution containing albumin.

DETAILED DESCRIPTION

The process of this invention provides for a simple and efficient procedure for the separation of albumin from an impure protein fraction which contains albumin and undesirable protein contaminants. The impure protein fraction used as the starting material for the albumin purification process may be the Fraction V paste from the Cohn method, other blood-plasma-derived fraction, or a composition provided by recombinant-DNA techniques.

In accordance with practice of this invention, high-purity albumin solutions are provided by removing protein contaminants from the impure protein fraction. The protein contaminants are removed by both precipitation of such contaminants from solutions containing the impure protein fraction and by adsorbing or binding additional contaminants that remain soluble, onto an anion-exchange resin. The solution containing the impure protein fraction, i.e., the first aqueous solution, is initially adjusted to a pH value where the charge on the albumin is close to zero, and where many contaminating proteins have no charge or a negative charge. Solution conditions found to be satisfactory for this step are a pH range of from about 4.5 to about 4.7 and a salt concentration below 40 Mm. Preferably, the pH of the solution is no less than about 4.5 nor greater than about 4.7, because, under these conditions, contaminating proteins, i.e., proteins other than albumin, are most effectively precipitated and can be removed by filtration. At a pH of less than about 4.5, more than the -desired amount of albumin precipitates, while at a pH of greater than about 4.7, less than the desired amount of contaminating proteins precipitate. Salt concentrations above about 40 mm are not desired because some contaminating proteins become more soluble as the salt concentration increases.

The combination of the pH value selected and the very low salt concentration of the first aqueous solution, results in precipitation of a portion of the contaminating proteins while albumin remains in solution. A "low salt concentration" as used herein, is a concentration less than about 40 Mm. Additional contaminating proteins, which are soluble under the solution conditions, are removed by binding them to an anion-exchange resin. Since albumin has a zero or slightly-positive charge in the pH range of from about 4.5 to about 4.7, it does not bind to the anion-exchange resin. The precipitated contaminants and anion-exchange resin-bound contaminants are separated from the aqueous solution to provide a second aqueous solution.

The process of precipitating insoluble contaminants and binding soluble contaminants to an anion-exchange resin is then repeated on the second aqueous solution by adjusting the pH of the second solution to a slightly-higher value than that of the first solution and by further reducing the salt concentration by ultrafiltration. Solution conditions found to be satisfactory for precipitation of contaminants from the second aqueous solution are a pH range of from about 4.7 to about 6.1 and a salt concentration below about 4 Mm. At a pH of less than about 4.7, the purification of albumin becomes less effective, as proteins that would be removed under such conditions have already been removed in the prior step at a similar pH. At a pH of more than about 6.1, the albumin, rather than the contaminating proteins, becomes more readily bound to the resin, and less than the desired amount of impurities precipitate. Salt concentrations above about 4 Mm are not desired because some contaminating proteins that are precipitated at a very low salt concentration, resolubilize. The pH of the second aqueous solution is preferably adjusted to from about 5.05 to about 5.15, and most preferably, is about 5.1. At these pH values, albumin exhibits a weak negative charge which allows it to bind to the anion-exchange resin. However, the contaminating proteins have a relatively-strong negative charge and will effectively compete with the albumin for the limited anion-exchange resin binding sites available.

The precipitated contaminants and the anion-exchange resin-bound contaminants, i.e., the contaminating proteins, are separated from the second aqueous solution to provide a third aqueous solution, which contains purified albumin. The purified albumin is recovered and, in an exemplary embodiment, is concentrated to provide a final purified albumin solution.

The purified albumin solution prepared by the procedure of this invention is of very high purity, i.e., greater than 99% of the protein present in the solution is albumin, while contaminants such as alpha-1-acid glycoprotein, alpha-1-antichymotrypsin, and retinol binding protein are not detectable. Also, purified albumin solutions provided in accordance with this invention have a relatively-high albumin monomer content, which can be greater than 93%, i.e., 93% of the albumin in the solution is monomer, while only about 6% of the albumin is present in the dimer or polymer form.

Any of a variety of anion-exchange resins can be used in accordance with this invention to bind soluble protein contaminants from the first and second aqueous solutions. Such resins include those sold under the trade names "DEAE-SEPHADEX," "DEAE-SEPHAROSE FF," and "Q-SEPHAROSE FF," by Pharmacia Company of Uppsala, Sweden, and "DE52 CELLULOSE," sold by Whatman International Ltd. of Maidstone, England. In one exemplary embodiment of practice of this invention, a diethylamino ethyl (DEAE) ligand bound to high-porosity, cross-linked dextran, DEAE-SEPHADEX A-50 resin, is used.

Two different ion-exchange-chromatography techniques can be used to bind soluble protein contaminants from the first and second aqueous solution in accordance with this invention. The first technique is called "column chromatography," and the second is called "batch chromatography." In column chromatography, an ion-exchange resin is packed into a column, and the solution which contains the proteins to be separated, is applied to the resin by pouring it through the resin at a rate that allows contaminating proteins to bind to the resin. The protein contaminants in the solution that do not have a charge appropriate for binding to the particular resin, pass through the column. The disadvantage of the column chromatography method is that the flow rate of liquids through the column is slow, and, therefore, time-consuming. This flow rate can be reduced even further if the material being applied to the column is particulate, as would result from the presence of precipitated proteins, since such particulate material can "clog" the resin to some degree.

When using batch chromatography, the ion-exchange resin is added directly to the protein solution, and the resin-protein mixture is gently agitated for a time sufficient to allow proteins to bind to the resin. The protein-bound-resin may then be removed by centrifugation or filtration, leaving unbound proteins in solution.

While both column and batch chromatography methods are applicable to the purification of albumin from Fraction V paste in accordance with this invention, batch purification is preferred due to the large volumes of protein solutions to be treated and the particulate nature of the solutions that result from the ph-precipitated contaminants. DEAE-SEPHADEX A-50 resin is preferred for such batch chromatography, since the ion-exchange resin is most conveniently discarded after use, thereby making the cost of the resin an important factor in the process. Based on the total binding capacity of DEAE-SEPHADEX A-50 resin and the required amount of ion-exchange resin, the yearly cost is substantially less when DEAE-SEPHADEX A-50 resin is used, compared to other commercially-available resins. Moreover, this resin has been studied extensively, is well documented, and accepted by the industrial and biological-science communities.

In an exemplary embodiment of practice of this invention, albumin is separated from Fraction V paste, prepared by the Cohn cold ethanol process. To purify albumin, the Fraction V paste recovered from the Cohn process is resuspended in from about 2 kg to about 5 kg of distilled water for each kg of paste, at from about 0° C. to about 10° C., to provide the first aqueous solution. Although more than 2 kg of water can be used per kg of Fraction V paste, 2 kg is preferred so that the total volume of the first aqueous solution is minimal, which in turn reduces the size and cost of the equipment required for the albumin purification process.

When the Fraction V paste is completely reconstituted, the pH of the first aqueous solution is adjusted to about 4.5 to about 4.7 by the addition of an acid, such as 2M acetic acid. A portion of the unwanted proteins become insoluble in this range and precipitate from solution. Additional protein contaminants, i.e., those that remain soluble at this pH range, are removed from the first aqueous solution by binding the protein contaminants to an anion-exchange resin, such as DEAE-SEPHADEX A-50 resin, DEAE-SEPHAROSE resin, Q-SEPHAROSE resin, or DE-52 CELLULOSE resin. In an exemplary embodiment, DEAE-SEPHADEX A-50, which is supplied in the form of a powder, is hydrated, as is described below in detail in Example 2, and the equivalent of from about 1.5 g to about 4.5 g, and preferably about 4 g, dry weight, of hydrated resin is added to the first aqueous solution for each kg of protein comprising the Fraction V paste. (The amount of protein in the Fraction V paste is determined by the commonly-known refractive index method.) The resin and solution are gently agitated for a selected time.

Contaminants with a PI below the pH of the first aqueous solution, i.e., below the 4.5 to 4.7 pH of the solution, will have a negative charge and will bind to the positively-charged resin during agitation. Some denatured albumin and contaminating proteins that promote the formation of albumin polymers are also bound to the resin. The precipitated contaminants and the DEAE-SEPHADEX A-50 resin-bound contaminants are separated from the first aqueous solution by filtration to provide a filtrate, i.e., the second aqueous solution.

The time required to bind the soluble protein contaminants to the anion-exchange resin is inversely proportional to the surface area of the resin. Therefore, shorter reaction times are required to bind the contaminants if larger resin volumes are used. Conversely, longer reaction times are required when smaller volumes of resin are used. In a preferred embodiment, relatively-small resin volumes are used, which significantly reduces the cost of the process, since the resin is discarded after use. Using relatively-smaller amounts of resin also simplifies the filtration operation that is used to remove both the contaminant-bound-resin and the precipitated contaminants. In an exemplary embodiment, when relatively-less resin is used, the time found sufficient to react the contaminants with the ion-exchange resin is from about 4 to about 5 hours.

In one exemplary embodiment, a filter aid, such as that sold under the trade name "CELITE 512" or "CELITE ANALYTICAL FILTER AID" (double-acid-washed CELITE) by Manville Products Corp. of Lompoc, Calif., is added to the first aqueous solution to promote separation of the precipitated contaminants and resin from the solution during the filtration operation. The CELITE can be satisfactorily employed at a concentration of from about 1.2 to about 2.5 grams per kg of the Fraction V paste starting material. After the addition of CELITE, the solution is mixed for 15 min. and then filtered at about 10° C., using a 10° C. and a 90SP, 0.4 to 0.6 micron filter, sold under the trade name "ZETA PLUS" by Cuno, Inc. of Meriden, Conn. The precipitated and resin-bound contaminants are retained on the filter while the albumin passes through the filter in the filtrate. The material that is retained on the filters is washed with distilled water to recover any small amounts of residual albumin remaining on the filters. If desired, 10% (vol/vol) ethanol may be added to the distilled water. The term "% (vol/vol)" as used herein, means the volume of material added (ethanol) per 100 ml of total solution. Distilled water containing 10% (vol/vol) ethanol is preferable to using a buffer, since a buffer may wash contaminants from the resin and into the albumin solution. The combined filtrate and wash solutions form the second aqueous solution.

In an exemplary embodiment, the second aqueous solution is washed twice by ultrafiltration, using an ultrafilter (or its equivalent) such as that supplied under the trade name of "MILLIPORE PELLICON" cassette 10K NMWL, by the Millipore Products Division of Millipore Corp., Bedford, Mass., in order to remove ethanol and any electrolytes that may be present. It is sufficient to use about 2.5 kg of distilled water per kg of second aqueous solution for the first wash. The second wash uses about 1.25 kg of distilled water per kg of second aqueous solution. During the washes, the temperature of the second aqueous solution is maintained below about 8° C. When the second wash is completed, the ultrafiltration system is rinsed with cold, distilled water, and the ultrafiltered and rinse solutions are combined. The combined total volume of the solution after the ultrafiltration wash is about the same as the original volume of the second aqueous solution.

The pH of the ultrafiltered second aqueous solution is increased to from about 4.7 to about 6.1, using an alkaline solution, such as 1M sodium hydroxide, to precipitate protein contaminants. In an exemplary embodiment, the pH is 5.1. At this increased pH, the negative charge on the contaminating proteins, which had a zero or weak negative charge in the first aqueous solution, will be increased. As a result of this increased negative charge, the contaminating proteins will have a higher affinity for the anion-exchange resin and will therefore bind to the resin and be removed from the second aqueous solution.

As was the case for the process of binding contaminants from the first aqueous solution, the equivalent of from about 1.5 g to about 4.5 g, and preferably about 4 g, dry weight, of hydrated DEAE-SEPHADEX A-50 resin per kg of protein comprising the Fraction V paste starting material is added to the second aqueous solution. The resin/second aqueous solution mixture is reacted by gently agitating for from about 4 hours to about 5 hours. CELITE 512 or CELITE ANALYTICAL FILTER AID is added to the DEAE-SEPHADEX A-50 resin/second aqueous solution mixture at a concentration of from about 1.2 to about 2.5 kg of CELITE 512 or CELITE ANALYTICAL FILTER AID per kg of Fraction V paste starting material. The mixture is filtered at 10° C., using ZETA PLUS 10C and 90SP, 0.4 to 0.6 micron, filters. The precipitated and resin-bound contaminants are retained on the filter while the albumin solution passes through the filter in the filtrate. The material that is retained on the filters is washed with distilled water to recover any small amounts of residual albumin remaining on the filters. Distilled water is preferable to using a buffer, since a buffer may wash contaminants from the resin. The filtrate and the wash solution are combined to form the third aqueous solution.

The third aqueous solution, which contains albumin, is then washed by ultrafiltration using a MILLIPORE PELLICON cassette 10K NMWL, or its equivalent, in order to remove electrolytes, as described above.

In an exemplary embodiment, the pH of the ultrafiltered solution is adjusted to from about 6.1 to about 6.3 with 1M sodium hydroxide, and the solution is concentrated to from 28% to 30% protein by ultrafiltration. The concentrated solution is stabilized by adding 0.08 mmole of N-acetyl-DL-tryptophan and 0.08 mmole of sodium caprylate per gram of protein.

Finally, the pH of the concentrated, stabilized albumin solution is adjusted to from about 6.8 to about 7.1 with 1M sodium hydroxide, the sodium concentration is adjusted to from about 130 to about 160 mEq per liter by the addition of sodium chloride, and the protein concentration is adjusted to from about 23.5 to about 26.5 g/100 ml by the addition of distilled water. The adjusted albumin solution is sterile-filtered on a 0.2 micron filter, supplied under the trade name "DURAPORE" by the Millipore Products Division of Millipore Corp., filled into the storage containers, pasteurized at 60° C. for 10 hours and incubated for 2 weeks at 30° C. The albumin solutions are then stored at not more than 37° C.

EXAMPLE 1

Preparation of Fraction V Paste

The pH of 3438 kg of human plasma was adjusted to about pH 7 using a 0.8M sodium acetate solution adjusted to a pH of 4.0 with acetic acid, and then mixed for 15 min. The pH 7 plasma was then brought to an ethanol concentration of 8% (vol/vol) by the addition of cold, about −15° C., 95% (vol/vol) ethanol. The temperature of the 8% ethanol solution was gradually reduced to from about −1° C. to about −3° C. as the cold ethanol solution was added. The 8% ethanol solution was mixed for about 15 min., during which time the Fraction I precipitated. The pH of the 8% ethanol solution was adjusted to 6.8 by the addition of a 0.8M sodium acetate solution adjusted to a pH of 4.0 with acetic acid. The resulting solution was mixed for about 15 min. and then brought to about 20% (vol/vol) ethanol by the addition of cold, about −15° C., 95% (vol/vol) ethanol. The temperature of the 20% ethanol solution was gradually reduced to from about −4° C. to about −6° C. as the cold ethanol solution was added. The 20% ethanol solution was mixed for about 60 min., during which time Fraction II+III precipitated. The Fractions I and II+III precipitates were removed by centrifugation and the supernatant retained. The pH of the 20% ethanol supernatant, which contained albumin, was then adjusted to 5.2 by the addition of a 0.8M sodium acetate solution adjusted to a pH of 4.0 with acetic acid, containing about 20% (vol/vol) ethanol. The resulting solution was mixed for about 2 hours at from about −4° C. to about −6° C., during which time the Fraction IV$_1$ precipitated. The pH was then adjusted to 5.8 with 1M sodium bicarbonate buffer, and mixing was continued for an additional 15 min. The 20% ethanol solution was then brought to about 40% ethanol (vol/vol) by the addition of cold, about −15° C., 95% ethanol (vol/vol). The addition of ethanol raised the pH to from about 5.9 to about 5.95. The 40% ethanol solution was mixed for 2 hours at from about −4° C. to about −6° C., during which time Fraction IV$_4$ precipitated. The Fractions IV$_1$ and IV$_4$ precipitates were removed by centrifugation, and the supernatant retained.

The 40% ethanol supernatant, which contained albumin, was processed further for the collection of the Fraction V precipitate. To precipitate Fraction V, the pH of the 40% ethanol supernatant was adjusted to 4.8 with a 0.8M sodium acetate solution adjusted to a pH of 4.0 with acetic acid, the temperature of the solution was reduced to from about −6° C. to about −12° C., and the solution was mixed for about 2 hours. The Fraction V precipitate, which contained albumin, was removed by centrifugation, and the resultant Fraction V paste was stored at −15° C. until required.

EXAMPLE 2

Preparation of DEAE-SEPHADEX A-50 Resin

In accordance with one exemplary embodiment of practice of this invention, each 4 grams of DEAE-SEPHADEX A-50 resin powder to be used per kg of protein comprising a Fraction V paste is hydrated by suspending it in 800 g of distilled water at a temperature of about 90° C. The suspension is mixed for 10 minutes, and then filtered on a 200-mesh stainless steel screen or sanitized nylon cloth. The resin is again resuspended in 800 g of distilled water at a temperature of about 90° C., mixed for an additional 10 minutes, and again filtered on a 200-mesh stainless steel screen or sanitized nylon. The DEAE-SEPHADEX A-50 resin is then resuspended in 800 g of distilled water, at a temperature of about 10° C., mixed for about 10 min., and filtered on a 200-mesh stainless steel screen or sanitized nylon. Finally, the resin is again resuspended in 800 g of distilled water at about 10° C., mixed for 10 min. and filtered on a 200-mesh stainless steel screen or sanitized nylon. The washed hydrated resin is used immediately.

The resin, washed in this manner, has a pH of about 4, and no further adjustment is required for subsequent use.

The volume of washed resin in distilled water is 2 to 3 times larger than resin treated in buffered solutions; thus, more binding sites on the resin surface and interior of the resin particles are exposed and available for binding contaminants. This higher volume results in a corresponding increase of from 60% to 1104 more reactive surface binding sites being available for binding contaminants. Therefore, hydrating the dry resin powder in water is preferred.

Examples 3-6 are directed to the separation of albumin from Fraction V paste using various anion-exchange resins.

EXAMPLE 3

Separation of Albumin from Fraction V Paste Using DEAE-SEPHADEX A-50 Resin

One kg of Fraction V paste, prepared in accordance with a process such as that described in Example 1, was mixed into 2 kg of distilled water at a temperature of 7° C., to provide the first aqueous solution. When the precipitate was completely reconstituted, the pH of the solution was adjusted to 4.62 with 2M acetic acid, and the protein concentration was adjusted to 9% by adding cold, distilled water. The amount of protein comprising the Fraction V paste was determined by refractive index to be 328 g.

A quantity of 1.31 grams of DEAE-SEPHADEX A-50 resin powder, which had been hydrated by a process such as that described in Example 2, was added to the first aqueous solution and gently agitated for 4 hours at 5° C. A quantity of 2.5 g of CELITE 512 powder per kg of Fraction V precipitate was added, and the solution was mixed for an additional 15 minutes. The suspension, which contained precipitated and DEAE-SEPHADEX A-50 resin-bound contaminants, was removed by filtering through ZETA PLUS 10C and 90SP, 0.4 and 0.2 micron membranes.

The precipitated and the resin-bound contaminants which were retained on the filter were then washed with 200 ml of 10% ethanol in distilled water per kg of Fraction V precipitate to recover any small amounts of residual albumin remaining in the filter-retained material. The wash solution and filtrate, which contained albumin, were combined to give the second aqueous solution.

The pH of the second aqueous solution was adjusted to about 5. 1 with 1M sodium hydroxide. The ph-adjusted second aqueous solution was washed twice, using ultrafiltration in a MILLIPORE PELLICON cassette 10K NMWL in order to remove ethanol and electrolytes. About 9 kg of distilled water were used in the wash during the first wash period, and the temperature was maintained at below 8° C. The solution was then concentrated by reducing its volume to one-half the volume of the second aqueous solution by ultrafiltration. The second wash was performed with about 9 kg of distilled water. When the second wash was completed, the ultrafiltration system was washed with cold, distilled water. The albumin-containing wash solution and filtrate, which contains albumin, were combined to form the ultrafiltered second aqueous solution.

A quantity of 0.98 gram of dried DEAE-SEPHADEX A-50 resin powder, hydrated by a process such as that described in Example 2, was added to the ultrafiltered second aqueous solution and gently agitated for 4 hours at 8° C. A quantity of 2.5 g of CELITE 512 powder was added per kg of Fraction V precipitate, and the solution was mixed for an additional 15 minutes.

The DEAE-SEPHADEX A-50 resin-bound contaminant/CELITE suspension was then filtered through ZETA PLUS 10C and 90SP, 0.4 and 0.2 micron membranes at 8° C. The precipitated and resin-bound contaminants that were retained on the filters were washed with 200 ml distilled water at a temperature of 7° C. to recover any small amounts of residual albumin remaining in the filter-retained suspension. The albumin-containing wash solution and filtrate were combined to provide a third aqueous solution, and the pH of the solution was adjusted to 6.19 with 1M sodium hydroxide. The ph-adjusted third aqueous solution was concentrated to 25.05% protein by ultrafiltration in a MILLIPORE PELLICON cassette 10K NMWL. The albumin concentrate was stabilized by the addition of 0.08 mmole of N-acetyl-DL-tryptophan and sodium caprylate per gram of protein. Finally, the pH was adjusted to 7.02 with 1M sodium hydroxide, the sodium concentration adjusted to 149 mEq per liter by the addition of sodium chloride, and the protein concentration adjusted to 24.4 g/100 ml. The final albumin-containing solution was sterile-filtered on a 0.2 micron filter, filled into storage containers, pasteurized at 60° C. for 10 hours, and then incubated for 2 weeks at 30° C. The purified albumin solutions were tested for the following:

1) Albumin polymers and aggregates were determined by zone electrophoresis in polyacrylamide, which separates ionic mixtures based on the electrophoretic mobilities of the constituent ions and their relative size. Separated monomeric, dimeric, and polymeric forms of albumin, in addition to fragments of albumin, are identified and quantitated. Alternative, monomeric, dimeric, and polymeric forms and fragments of albumin may be separated by HPLC;
2) Heme content was measured by determination of the absorbance of the solution at 403 nm wavelength using a UV spectrophotometer, Model DV-6, supplied by Beckman Instruments, Inc. of Fullerton, Calif.;
3) Purity of the albumin solutions was determined using cellulose acetate membrane electrophoresis;
4) Prekallikrein Activator (PKA) concentrations were determined by chromogenic assay comparisons to an Office of Biologics standard;
5) Heat stability was determined by visual inspection and nephelometric readings following the heating cycle at 60° C.±0.5° C. for 10 hours of one sample and heating for an additional 50 hours at 57° C. on a second sample;
6) alpha-1-acid glycoprotein was determined by radial immunodiffusion method using sheep antibodies supplied by The Binding Site Ltd. of Birmingham, England; and
7) Particle counts were determined by HIAC Analyzer, Model #PC-320, supplied by the HIAC Instruments Division of Pacific Scientific, Menlo Park, Calif.

The properties of the purified albumin solutions obtained are summarized in Table 1.

EXAMPLE 4

Separation of Albumin from Fraction V Paste Using DEAE-SEPHAROSE Resin

The procedure of this example is the same as the procedure of Example 3, except that 120 ml of DEAE-SEPHAROSE resin per kg of protein in the Fraction V paste was used in place of DEAE-SEPHADEX A-50 resin. The DEAE-SEPHAROSE resin was prepared by washing in distilled water. This procedure was carried out in duplicate, and the results of both separation procedures using DEAE-SEPHAROSE resin are summarized in Table 1.

EXAMPLE 5

Separation of Albumin from Fraction V Paste Using Q-SEPHAROSE Resin

The procedure of this example is the same as the procedure of Example 3, except that 80 ml of Q-SEPHAROSE resin per kg of protein in the Fraction V paste was used in place of DEAE-SEPHADEX A-50 resin. The Q-SEPHAROSE resin was prepared by washing in distilled water. This procedure was carried out in duplicate, and the results of both separation procedures using Q-SEPHAROSE resin, are summarized in Table 1.

EXAMPLE 6

Separation of Albumin from Fraction V Paste Using DE-52 CELLULOSE Resin

The procedure of this example is the same as the procedure of Example 3, except that 74 ml of DE-52 CELLULOSE resin per kg of protein in the Fraction V paste was used in place of DEAE-SEPHADEX A-50 resin. The DE-52 CELLULOSE resin was prepared by washing in distilled water. The procedure was carried out in duplicate, and the results of both separation procedures using DE-52 CELLULOSE resin, are summarized in Table 1.

TABLE 1

| | Example 3 | Example 4 | | Example 5 | | Example 6 | |
|---|---|---|---|---|---|---|---|
| Type of Ion-Exchange Medium | DEAE-SEPHADEX | DEAE-SEPHAROSE | DEAE-SEPHAROSE | Q-SEPHAROSE | Q-SEPHAROSE | DE-52 CELLU. | DE-52 CELLU. |
| Amount of Resin Used | 4 g/3 g* | 120/120** | 120/120** | 80/80** | 80/80** | 74/74** | 74/74** |
| Purity, % | | | | | | | |
| Albumin | 99.6 | 97.85 | 97.95 | 97.60 | 97.60 | 96.40 | 98.65 |
| alpha-Globulins | 0.4 | 2.15 | 2.05 | 2.40 | 2.40 | 3.60 | 1.35 |
| Monomer Content, % | | | | | | | |
| monomer | 92.89 | 90.3 | 91.6 | 90.8 | 90.3 | 90.5 | 91.3 |
| dimer | 1.45 | 1.2 | 1.1 | 1.3 | 1.3 | 1.2 | 1.2 |
| polymer | 5.66 | 6.2 | 5.0 | 5.6 | 6.2 | 6.1 | 5.1 |

TABLE 1-continued

|  | Example 3 | Example 4 | Example 5 | | Example 6 | |
| --- | --- | --- | --- | --- | --- | --- |
| fragment | NA | 2.3 | 2.3 | 2.2 | 2.2 | 2.4 |
| Heat Stability, NU. | | | | | | |
| 10 hrs/60° C. | 2.5 | 3.0 | 2.9 | 2.4 | 3.7 | 3.6 | 3.3 |
| 50 hrs/57° C. | 3.1 | 3.7 | 2.8 | 3.2 | 4.4 | 4.4 | 3.8 |
| Particle Count/ml | | | | | | |
| 2 um | 61 | 125 | 176 | 130 | 251 | 114 | 129 |
| 5 um | 14 | 23 | 19 | 21 | 15 | 13 | 13 |
| 10 um | 3 | 3 | 1 | 4 | 2 | 3 | 3 |
| Visual Observation | Clear | Clear | Clear | Clear | Clear | Clear | Clear |
| Contaminants | | | | | | |
| Heme, Absorbance at 403 nm | NA | 0.057 | 0.042 | 0.042 | 0.060 | 0.056 | 0.044 |
| alpha-1-acid glycoprotein | NA | ND | ND | ND | ND | ND | ND |
| Prekallikrein Activator, % | ND | 0.24 | ND | ND | 0.36 | ND | ND |

*g of resin (dry weight) per kg of protein in the Fraction V paste added to first aqueous solution/second aqueous solution
**ml of resin added per kg of protein in the Fraction V paste to first aqueous solution/second aqueous solution
NU = Nephelometric Unit
NA = Not Available
ND = None Detected (The detection limit for alpha-1-acid glycoprotein is 18 mg/dl, and for Prekallikrein Activator is 0%.

The results summarized in Table 1 show that the purity, the monomer content and the clarity of the albumin prepared in accordance with the process of this invention, using DEAE-SEPHADEX A-50 resin, DEAE-SEPHAROSE resin, Q-SEPHAROSE resin, and DE-52 CELLULOSE resin, were essentially the same.

EXAMPLE 7

Pilot Plant Scale-Up Purification of Albumin

Approximately 4 kg of Fraction V paste, prepared in accordance with a process such as that described in Example 1, was suspended in 8 kg of distilled water at 6.5° C. to provide the first aqueous solution. When the precipitate was completely reconstituted, the pH of the solution was adjusted to 4.64 with 2M acetic acid, and the protein concentration was adjusted to 9% by adding cold, distilled water. The amount of protein comprising the Fraction V paste was determined by refractive index to be 1377.5 g.

Four grams of dried DEAE-SEPHADEX A-50 resin powder per kg of protein in the Fraction V paste, i.e., 5.51 g of DEAE-SEPHADEX A-50 resin powder, hydrated by a process such as that described in Example 2, was added to the first aqueous solution and gently agitated for 4 hours at 3° C. Ten grams of CELITE 512 powder were added, and the solution was mixed for an additional 15 minutes. The suspension, which contained precipitated and DEAE-SEPHADEX A-50 resin-bound contaminants, was removed by filtering through ZETA PLUS 10C and 90SP, 0.4 and 0.2 micron membranes.

The precipitated and the resin-bound contaminants retained on the filters were washed with about 800 ml of 10% ethanol/water to recover any small amounts of residual albumin remaining in the filter-retained material. The albumin-containing wash solution and filtrate were combined to provide a second aqueous solution.

The pH of the second aqueous solution was adjusted to about 5.1 with 1M sodium hydroxide. The ph-adjusted second aqueous solution was then washed using ultrafiltration in a MILLIPORE PELLICON cassette 10K NMWL to remove the ethanol and electrolytes. Approximately 40 kg of distilled water was used in the washing during the first washing period, and the temperature was maintained at below 8° C. The second wash was performed using about 40 kg of distilled water. When the second wash was completed, the ultrafiltration system was washed with cold, distilled water. The albumin-containing wash solution and filtrate were combined to form the ultrafiltered second aqueous solution.

Three grams of dried DEAE-SEPHADEX A-50 resin powder per kg of protein in the Fraction V paste, i.e., 4.13 g of DEAE-SEPHADEX A-50 resin powder, were hydrated by a process such as that described in Example 2 and added to the ultrafiltrated solution, which was gently agitated for 4 hours at 5° C. Ten grams of CELITE 512 powder or CELITE ANALYTICAL FILTER AID were added, and the solution was mixed for an additional 15 minutes.

The DEAE-SEPHADEX A-50 resin-bound contaminant/CELITE suspension was then filtered through ZETA PLUS 10C and 90SP, 0.4 and 0.2 micron membranes, at 5° C. The precipitated and resin-bound contaminants which were retained by the filters were washed with 800 ml distilled water at a temperature of 5° C., to recover any small amounts of residual albumin remaining in the filter-retained material. The albumin-containing wash solution and filtrate were combined to provide a third aqueous solution, and the pH was adjusted to 6.19 with 1M sodium hydroxide.

The ph-adjusted third aqueous solution was concentrated to 26.75% protein by ultrafiltration in a MILLIPORE PELLICON cassette 10K NMWL, as described above. The concentrate was stabilized by the addition of 0.08 mmole of N-acetyl-DL-tryptophan and sodium caprylate per gram of protein. Finally, the pH was adjusted to 6.9 with 1M sodium hydroxide, the sodium concentration adjusted to 144 mEq per liter by the addition of sodium chloride, and the protein concentration adjusted to 25.0 g/100 ml. The final albumin-containing solution was sterile-filtered on a 0.2 micron filter, filled into storage containers, pasteurized at 60° C. for 10 hours, and then incubated for 2 weeks at 30° C.

The methods used to analyze the purified albumin preparations are described in Example 3. In addition, the purified albumin solutions were tested for the following:

1) Prealbumin was determined by radial immunodiffusion method using goat or horse antibodies supplied by Behring Diagnostics, Inc. of Somerville, N.J.;

2) alpha-1-antitrypsin was determined by radial immunodiffusion method using sheep antibodies supplied by The Binding Site Ltd.;
3) alpha-1-antichymotrypsin was determined by radial immunodiffusion method using sheep antibodies supplied by The Binding Site Ltd.;
4) Ceruloplasmin was determined by radial immunodiffusion method using rabbit antibodies supplied by Behring Diagnostics, Inc., or sheep antibodies supplied by The Binding Site Ltd.;
5) Retinol binding protein was determined by radial immunodiffusion method using rabbit antibodies supplied by Behring Diagnostics, Inc.;
6) Haptoglobin was determined by radial immunodiffusion method using sheep antibodies supplied by The Binding Site Ltd.; and
7) Transferrin was determined by radial immunodiffusion method using sheep antibodies supplied by The Binding Site Ltd.

This procedure was repeated an additional 3 times (except that, in runs 2-4, 4 g of dried DEAE-SEPHADEX A-50 resin powder was added to the second solution per kg of protein in the Fraction V paste starting material), and the properties of the purified albumin solution prepared from each of the 4 procedures are summarized in Table 2.

TABLE 2

|  | Run 1 | Run 2 | Run 3 | Run 4 |
|---|---|---|---|---|
| Fr V Paste Sample, Kg | 4.0 | 3.9 | 3.9 | 4.0 |
| Purity, % |  |  |  |  |
| Albumin | 99.9 | 99.6 | 99.2 | 99.4 |
| alpha-Globulins | 1.0 | 0.4 | 0.8 | 0.6 |
| Monomer Content, % |  |  |  |  |
| monomer | 90.85 | 93.63 | 93.24 | 93.20 |
| dimer | 0.82 | 0.97 | 1.27 | 1.61 |
| polymer | 6.99 | 3.90 | 3.92 | 3.50 |
| fragment | 1.33 | 1.49 | 1.56 | 1.69 |
| Heat Stability, NU, |  |  |  |  |
| 10 hrs/60° C. | 3.0 | 2.0 | 2.0 | 2.3 |
| 50 hrs/57° C. | 3.3 | 2.3 | 2.2 | 2.6 |
| Contaminants, mg/dL |  |  |  |  |
| Prekallikrein Activator, % | ND | ND | ND | ND |
| Heme, Absorbance at 403 nm | 0.057 | 0.044 | 0.044 | 0.044 |
| Prealbumin | 35 | 39 | 38 | 36 |
| alpha-1-acid glycoprotein | ND | ND | ND | ND |
| alpha-1-antitrypsin | ND | ND | ND | ND |
| alpha-1-antichymotrypsin | ND | ND | ND | ND |
| Ceruloplasmin | 8 | ND | ND | ND |
| Retinol binding protein | ND | ND | ND | ND |
| alpha-2-HS glycoprotein | 10 | 13 | 11 | 12 |
| Haptoglobin | 34 | 22 | 24 | 27 |
| Transferrin | 8 | 9 | 8 | 6 |

NU = Nephelometric Unit
ND = None Detected (The detection limits of the contaminants are as follows: Prekallikrein Activator, is 0%; alpah-1-acid glycoprotein, 1.4 mg/dl; alpha-1-antitrypsin, 1.8 mg/dl; alpha-1-antichymotrypsin, 2 mg/dl; Ceruloplasmin, 1.4 mg/dl; and Retinol binding protein, 0.5 mg/dl.)

The results summarized in Table 2 show that in all the pilot plant scale-up experiments, albumin was of high purity, greater than 99%, and contaminants, such as alpha-1-acid glycoprotein, alpha-1-antitrypsin, alpha-1-antichymotrypsin, and retinol binding protein, were not detected in the purified albumin solution. Also, the albumin monomer content of the purified albumin solutions was found to be from 90% (wt/wt) to over 93% (wt/wt) of the total albumin.

EXAMPLE 8

Large-Scale Purification of Albumin

A quantity of about 200 kg of Fraction V precipitate, prepared in accordance with a process such as that described in Example 1, was suspended in 412 kg of distilled water at a temperature of about 3° C. to provide the first aqueous solution. When the precipitate was completely reconstituted, the pH of the first aqueous solution was adjusted to 4.63 with 2M acetic acid, and the protein concentration adjusted to 9% by adding cold, distilled water.

A quantity of 260.5 g of dry DEAE-SEPHADEX A-50 resin powder was hydrated by a process such as that described in Example 2, added to the first aqueous solution, and gently agitated for 4 hours at from about 1.4° C. to about 3.1° C. A quantity of 515 grams of acid-washed CELITE 512 powder or CELITE ANALYTICAL FILTER AID was added, and the solution mixed for an additional 15 minutes. The suspension, which contained precipitated and DEAE-SEPHADEX A-50 resin-bound contaminants, was filtered through ZETA PLUS 10C and 90SP, 0.4 and 0.2 micron membranes.

The precipitated and the resin-bound contaminants retained on the filters were washed with 41 kg of 10% ethanol/water to recover any small amounts of residual albumin remaining in the filter-retained material. The albumin-containing wash solution and filtrate were combined to provide a second aqueous solution.

The pH of the second aqueous solution was adjusted to about 5.1 with 1M sodium hydroxide. The ph-adjusted second aqueous solution was washed using ultrafiltration in a MILLIPORE PELLICON cassette 10K NMWL in order to remove the ethanol and electrolytes. A quantity of 1955 kg of distilled water was used in the washing of the pH-adjusted second aqueous solution during the first wash period, the temperature of which was maintained at below 8° C. The second wash was performed with 1955 kg of distilled water. When the second wash was completed, the ultrafiltration system was washed with 391 kg of cold, distilled water. The albumin-containing wash solution and filtrate were combined to form the ultrafiltered second aqueous solution.

A quantity of 206.5 g of dry DEAE-SEPHADEX A-50 resin powder was hydrated by a process such as that described in Example 2, and added to the ultrafiltrated second aqueous solution, and gently agitated 4 hours at from about 1.7° C. to about 3.8° C. A quantity of 515 g of acid-washed CELITE 512 powder or CELITE ANALYTICAL FILTER AID was added, and the solution was mixed for an additional 15 minutes.

The DEAE-SEPHADEX A-50 resin-bound contaminant/CELITE suspension was then filtered through ZETA PLUS 10C and 90SP, 0.4 and 0.2 micron membranes at from about 3.1° C. to about 4.0° C. The precipitated and resin-bound contaminants that were retained on the filters were washed with 41 kg of distilled water, at a temperature of 6.9° C., to recover any small amounts of residual albumin remaining in the filter-retained material. The albumin-containing wash solution and filtrate were combined to provide a third aqueous solution, and the pH was adjusted to 6.23 with 1M sodium hydroxide.

The third aqueous solution was concentrated to 26.05% protein by ultrafiltration in a MILLIPORE PELLICON cassette 10K NMWL, as described above. The concentration was stabilized by the addition of 0.08 mmole of N-acetyl-DL-tryptophan and sodium caprylate per gram of protein. Finally, the pH was adjusted to 6.93 with 1M sodium hydroxide, the sodium concentration adjusted to 146 mEq per liter by the addition of sodium chloride, and the protein concentration adjusted to 24.2 g/100 ml. The final albumin-containing solution was sterile-filtered on a 0.2 micron filter, filled into storage containers, pasteurized at 60° C. for 10 hours, and then incubated for 2 weeks at 30° C.

The methods used to analyze the purified albumin preparation are as described in Examples 3 and 7.

This procedure was repeated an additional 2 times, and the properties of the purified albumin solution from each of the 3 separation procedures are summarized in Table 3.

TABLE 3

|  | Run 1 | Run 2 | Run 3 |
| --- | --- | --- | --- |
| Fr V Paste Sample, Kg | 206 | 198.9 | 203.9 |
| Purity, % | | | |
| Albumin | 98 | 98.5 | 100 |
| alpha-Globulins | 2 | 1.5 | 0 |
| Monomer Content, % | | | |
| monomer | 91.7 | 93.7 | 90.6 |
| dimer | 1 | 0.9 | 2.4 |
| polymer | 5.5 | 5.1 | 5.6 |
| fragment | 1.8 | 0.3 | 1.4 |
| Heat Stability, NU, | | | |
| 10 hrs/60° C. | <7 | <7 | <7 |
| 50 hrs/57° C. | <7 | <7 | <7 |
| Contaminants, mg/dL | | | |
| Prekallikrein Activator, % | ND | ND | ND |
| Heme, Absorbance at 403 nm | 0.059 | 0.046 | 0.060 |
| Prealbumin | 37 | 38 | 38 |
| alpha-1-acid glycoprotein | ND | ND | ND |
| alpha-1-antichymotrypsin | ND | ND | ND |
| Retinol binding protein | ND | ND | ND |
| alpha-2-HS glycoprotein | 13 | 13 | 10 |
| Ceruloplasmin | ND | ND | ND |
| Particle Count | | | |
| >2 um | 41 | 120 | 81 |
| >5 um | 8 | 23 | 17 |
| >10 um | 2 | 5 | 5 |
| >25 um | 1 | 0 | 0 |
| >50 um | 0 | 0 | 0 |

NU = Nephelometric Unit
ND = None Detected (The detection limits of the contaminants are as follows: Prekallikrein Activator, is 0%; alpah-1-acid glycoprotein, 1.0 mg/dl; alpha-1-antichymotrypsin, 3 mg/dl; Ceruloplasmin, 2 mg/dl; and Retinol binding protein, 0.5 mg/dl.)

The results summarized in Table 3 show that the albumin, purified in the large-scale purification of albumin, was free of detectable contamination by alpha-1-acid glycoprotein, alpha-1-antichymotrypsin, and retinol binding protein. The monomer content ranged between 90.6% and 93.7% of the total albumin concentration. The purity of the albumin was found to be between 98% and 100%. Also, the particle count for particles of a size greater than 10 um was very low, or zero, and for smaller particles, in the range of from 2 um to 5 um, the particle count was also low. The results show that albumin, purified on a large scale using precipitation and adsorption of contaminants onto DEAE-SEPHADEX A-50 resin has a high purity, a high monomer content, and a high clarity and solubility (as indicated by the low particle count).

EXAMPLE 9

Acetone and Heat-Shock Purification of Albumin

A method previously used for the preparation of albumin solutions incorporates acetone precipitation and heat-shock to remove contaminants. An example of the acetone/heat-shock method is provided so that the results obtained with this method can be compared to the improved process of this invention. A quantity of 228.4 kg of Fraction V paste was dissolved in 2.642 gallons of acetone per kg of Fraction V paste at −20° C. or colder. After the paste was resuspended in the acetone, the solution was mixed for 4 hours to solubilize contaminants. The suspension was then filtered and washed with acetone. The retentate, the acetone "cake" which contained albumin, was dried under a nitrogen stream at a temperature of 25° C. using the fluid bed dryer.

The dried acetone powder was then resuspended in water to a concentration of 7% albumin at 10° C. The pH of the 7% albumin solution was adjusted to 6.38 with 1M sodium hydroxide. Any particulate matter that was present in the solution was then removed by filtration, using ZETA PLUS CPX 10C and CPX 90S filters. A quantity of 200 g of CELITE 512 was added to aid filtration.

After filtration, the falters were washed with distilled water at a temperature of 7° C. The filtrate, which contained albumin, and the wash solutions were combined and washed using a MILLIPORE PELLICON cassette ultrafiltration device, to remove salts. The ultrafiltered solution was then concentrated by ultrafiltration to a final protein concentration of approximately 15%.

The concentrated albumin solution was adjusted to a pH of 6.8 by the addition of 0.5M sodium hydroxide, and stabilized by the addition of 0.08 mmole sodium caprylate and 0.08 mmole N-acetyl-tryptophan per gram of protein. The stabilized albumin solution was filtered, using a 0.4 micron membrane filter, sold under the trade name "CWSS" by the Millipore Products Division of Millipore Corp., and a 0.2 DURAPORE filter, to remove any particulate matter. The filters were washed with cold, distilled water to remove any trapped albumin.

Heat-shocking of the stabilized albumin solution was then performed for 2 hours at 60° C., using a circulating glycerol heating system. After the 2-hour heat-shock, the solution was chilled to 9° C.

The heat-shocked solution was filtered through a ZETA PLUS CPX 90S filter to remove precipitated and particulate matter that formed as a result of the heat-shock treatment. The filter was washed with distilled water at a temperature of 7° C. The filtrate, which contained albumin, and the wash solution were combined.

The filtered heat-shocked solution was then concentrated by ultrafiltration to from 28% to 30% protein. The sodium caprylate and tryptophan concentrations were each adjusted to 0.08 mmole per gram of protein, the pH of the solution was adjusted to 6.9 using 0.5M sodium hydroxide, and the sodium ion concentration was adjusted to 145 mEq per liter by the addition of sodium chloride. The solution was then sterile-filtered and distributed into storage vials.

The methods used to analyze the purified albumin preparations are as described in Examples 3 and 8.

TABLE 4

|  | Example 9 |
| --- | --- |
| Purity, % | |
| Albumin | 97.8 |

TABLE 4-continued

|  | Example 9 |
|---|---|
| alpha-Globulins | 2.2 |
| Monomer Content, % | |
| monomer | 87.5 |
| dimer | 2.1 |
| polymer | 9.8 |
| N-mer | 0.3 |
| fragment | 0.3 |
| Contaminants, mg/dL | |
| Prealbumin | 65 |
| alpha-1-acid glycoprotein | 55 |
| alpha-1-antichymotrypsin | 9 |
| Retinol binding protein | 2 |
| alpha-2-HS glycoprotein | 29 |
| Haptoglobin | 48 |
| Particle Count | |
| >2 um | 283 |
| >5 um | 88 |
| >10 um | 15 |
| >25 um | 1 |
| >50 um | 0 |

The results in Table 4 show that albumin prepared by acetone and heat-shock treatments had a purity of 97.8% and, also, had detectable levels of the contaminants alpha-1-acid glycoprotein, alpha-1-antichymotrypsin, and retinol binding protein. The monomer content of the sample was approximately 87% of the total albumin in the sample. Particle counts were 283 particles per ml that are greater than 2 microns.

EXAMPLE 10

Comparison of Albumin Prepared by Different Preparation Methods

To show the advantages of purifying albumin in accordance with the process of this invention, a comparison was made among albumin preparations purified by the precipitation/DEAE-SEPHADEX adsorption method of this invention (Example 8), those prepared by the prior-art acetone/heat-shock method (Example 9), and other commercially-available preparations of albumin.

Albumin purified in accordance with the process of Example 8 has undetectable levels of alpha-1-acid glycoprotein, alpha-1-antichymotrypsin, and retinol binding protein (data shown in Table 5). Conversely, albumin preparations purified in accordance with the acetone/heatshock method of Example 9 include significant amounts of contaminating proteins, such as 55 mg/dl of alpha-1-acid glycoprotein, 9 mg/dl of alpha-1-antichymotrypsin, and 2 mg/dl of retinol binding protein (data shown in Table 5). In various commercial preparations, the level of alpha-1-acid glycoprotein has been found to be from 49 mg/dl to 11 mg/dl, the level of alpha-1-antichymotrypsin, from 8 mg/dl to 6 mg/dl, and the level of retinol binding protein, from 3 mg/dl to 1 mg/dl. Thus, the purity of albumin prepared by the process of this invention is enhanced.

TABLE 5

|  |  |  | Example 8 | Example 9 |
|---|---|---|---|---|
| Purity, %, Albumin | 98 | 98.5 | 100 | 97.8 |
| Monomer Content, % | | | | |
| monomer | 91.7 | 93.7 | 90.6 | 87.5 |
| dimer | 1 | 0.9 | 2.4 | 2.1 |
| polymer | 5.5 | 5.1 | 5.6 | 9.8 |
| fragment | 1.8 | 0.3 | 1.4 | 0.3 |
| Contaminants, mg/dL | | | | |
| Prealbumin | 37 | 38 | 38 | 65 |
| alpha-1-acid glycoprotein | ND | ND | ND | 55 |
| alpha-1-antitrypsin | ND | ND | ND | ND |
| alpha-1-antichymotrypsin | ND | ND | ND | 9 |
| Retinol binding protein | ND | ND | ND | 2 |
| alpha-2-HS glycoprotein | 13 | 13 | 10 | 29 |
| Particle Count | | | | |
| >2 um | 41 | 120 | 81 | 283 |
| >5 um | 8 | 23 | 17 | 88 |
| >10 um | 2 | 5 | 5 | 15 |
| >25 um | 1 | 0 | 0 | 1 |
| >50 um | 0 | 0 | 0 | 0 |

ND = None Detected (The detection limits of the contaminants are as follows: alpah-1-acid glycoprotein, 1.8 mg/dl; alpha-1-antitrypsin, 1.5 mg/dl; alpha-1-antichymotrypsin, 3 mg/dl; and Retinol binding protein, 0.5 mg/dl.)

Albumin purified by practice of the process of this invention also exhibits high clarity (due to the low particle count in the albumin preparations). The particle count of the albumin prepared in accordance with Example 8 is between 41 and 120 for particles in the 2 um range and between 0 and 5 for particles in the greater-than-10 uM range. In albumin preparations purified by acetone/heat-shock method of Example 9, the average particle count is 557 for particles in the 2 um range and about 13 for particles in the greater-than-10 um range. Commercial preparations have been found to have particle counts of between 3796 and 345 for particles in the 2 um range and 40 to 0 for particles in the greater-than-10 um range. As a result of the low particle count, the albumin concentrates prepared in accordance with the process of this invention have a high clarity.

In addition to the high purity and clarity of the albumin prepared in accordance with the process of this invention, albumin monomer contents were at least equal to, if not higher than, those found in other commercial preparations.

The high monomer content of the albumin prepared in accordance with the practice of this invention, combined with the high purity and clarity of the preparations, account for the significant improvement over albumin prepared by other methods.

The above descriptions of exemplary embodiments of processes for producing albumin are for illustrative purposes. Because of variations which will be apparent to those skilled in the art, the present invention is not intended to be limited to the particular embodiments described above. The scope of the invention is defined by the following claims.

What is claimed is:

1. A process for separating albumin from an impure protein fraction comprising albumin and unwanted protein contaminants, the process comprising the steps of:
   a) providing a first aqueous solution containing the impure protein fraction;
   b) adjusting the pH of the first aqueous solution to a value of from about 4.5 to about 4.7 to precipitate protein contaminants; and
   c) purifying the albumin further by ion-exchange chromatography, wherein the ion-exchange chromatography steps consist essentially of:
      binding soluble protein contaminants in the first aqueous solution to an anion-exchange resin;
      separating the precipitated contaminants and the anion-exchange resin-bound contaminants from the first aqueous solution to provide a second aqueous solution containing albumin;

adjusting the pH of the second aqueous solution to a value of from 5.0 to about 6.1 to precipitate protein contaminants;

binding additional soluble protein contaminants in the second aqueous solution to an anion-exchange resin; and separating the precipitated contaminants and the anion-exchange resin-bound contaminants from the second aqueous solution to provide a third aqueous solution containing albumin.

2. The process of claim 1 wherein the first aqueous solution has a salt concentration of less than about 40 mM.

3. The process of claim 1 wherein the first aqueous solution has a salt concentration of less than about 4 mM.

4. The process of claim 1 wherein the first and second aqueous solutions are maintained at a temperature of from about 0° C. to about 10° C. during the precipitation and resin-binding steps.

5. The process of claim 1 wherein the pH of the first aqueous solution is adjusted to about 4.6 to precipitate protein contaminants.

6. The process of claim 1 wherein the anion-exchange resin used to bind soluble contaminants in the first aqueous solution is a diethylamino ethyl ligand bound to a cross-linked dextran matrix.

7. The process of claim 1 wherein the anion-exchange resin is added to the first aqueous solution to bind soluble contaminants.

8. The process of claim 1 wherein the soluble contaminants in the first aqueous solution are bound to the anion-exchange resin by flowing the solution through such a resin contained in a chromatographic column.

9. The process of claim 1 wherein albumin is washed from the anion-exchange resin after binding soluble contaminants from the first aqueous solution a solution containing a salt concentration of less than 40 mM.

10. The process of claim 1 wherein albumin is washed from the anion-exchange resin after binding soluble contaminants from the first aqueous solution with a solution of water containing about 10% (vol/vol) ethanol.

11. The process of claim 1 wherein the pH of the second aqueous solution is adjusted to a value of from 5 to about 5.2 to precipitate protein contaminants.

12. The process of claim 11 wherein the pH of the second aqueous solution is adjusted to a value of 5.1 to precipitate protein contaminants.

13. The process of claim 1 wherein the anion-exchange resin used to bind soluble contaminants in the second aqueous solution is a diethylanino ethyl ligand bound to a cross-linked dextran matrix.

14. The process of claim 1 wherein the anion-exchange resin is added to the second aqueous solution to bind soluble contaminants.

15. The process of claim 1 wherein the soluble contaminants in the second aqueous solution are bound to the anion-exchange resin by flowing the solution through the resin contained in a chromatographic column.

16. The process of claim 1 wherein albumin is washed with water from the anion-exchange resin after soluble contaminants in the second aqueous solution are bound to the resin.

* * * * *

UNITED STATES PATENT AND TRADEMARK OFFICE
CERTIFICATE OF CORRECTION

PATENT NO. : 5,250,662
DATED : October 5, 1993
INVENTOR(S) : Chong E. Chang

It is certified that error appears in the above-indentified patent and that said Letters Patent is hereby corrected as shown below:

Column 2, line 40, change "PH" to -- pH --.

Column 3, line 32, change "mm" to -- mM --.

Column 4, line 40, change 40Mm" to -- 40mM --.
Column 4, line 45, change "-desired" to -- desired --.
Column 4, line 49, change "40mm" to -- 40 mM --.
Column 4, line 57, change "40 Mm" to -- 40 mM --.

Column 5, line 7, change "4 Mm" to -- 4 mM --.
Column 5, line 15, change "4 Mm" to -- 4 mM --.

Column 6, line 19, change "ph" to -- pH --.
Column 6, line 65, change "PI" to -- pI --.

Column 7, line 35, change "10°C." to -- 10C --.
Column 7, line 43, change "104" to -- 10% --.

Column 8, line 35, change "Contaminants" to
          -- contaminants --.
Column 8, line 45, change "3 0%" to -- 30% --.

Column 10, line 13, change "1104" to -- 110% --.
Column 10, line 56, change "5. 1" to -- 5.1 --.
Column 10, line 56, change "ph" to -- pH --.

Column 11, line 22, change "ph" to -- pH --.

UNITED STATES PATENT AND TRADEMARK OFFICE
CERTIFICATE OF CORRECTION

PATENT NO. : 5,250,662
DATED : October 5, 1993
INVENTOR(S) : Chong E. Chang

It is certified that error appears in the above-indentified patent and that said Letters Patent is hereby corrected as shown below:

Column 13, lines 10-12, in Table 1, change "um" to -- $\mu$m -- (all occurrences).
Column 13, line 61, change "ph" to -- pH --.

Column 14, line 48, change "ph" to -- pH --.

Column 15, line 33, in Table 2, after "Albumin" and under "Run 1" change "99.9" to -- 99.0 --.

Column 16, line 33, change "ph" to -- pH --.

Column 17, lines 39-42, in Table 3, change "um" to -- $\mu$m -- (all occurrences).
Column 17, lines 56,57, change "um" to -- $\mu$m -- (all occurrences).

Column 18, line 23, change "f alters" to -- filters --.
Column 18, line 64, before "Table 4" insert -- The results are summarized in Table 4. --.

Column 19, lines 18-21, in Table 4, change "um" to -- $\mu$m -- (all occurrences).

Column 20, lines 11-14, in Table 5, change "um" to -- $\mu$m -- (all occurrences).
Column 20, line 16, change "alpah" to -- alpha --.
Column 20, lines 23,25,27,28,31,32, change "um" to -- $\mu$m -- (all occurrences).

UNITED STATES PATENT AND TRADEMARK OFFICE
CERTIFICATE OF CORRECTION

PATENT NO. : 5,250,662
DATED : October 5, 1993
INVENTOR(S) : Chong E. Chang

It is certified that error appears in the above-indentified patent and that said Letters Patent is hereby corrected as shown below:

In the Claims:

Column 21, line 4, before "6.1 to" delete "about".

Column 22, line 5, change "solution a solution" to
-- solution using a solution --.

Column 22, line 20, change "diethylanino" to
-- diethylamino --.

Signed and Sealed this

Twenty-sixth Day of July, 1994

Attest:

BRUCE LEHMAN

Attesting Officer    Commissioner of Patents and Trademarks